United States Patent
Nylander et al.

(10) Patent No.: US 8,627,710 B2
(45) Date of Patent: Jan. 14, 2014

(54) GAS PROBE FOR SAMPLING GAS MOLECULES FROM A FLUID AND A SYSTEM COMPRISING THE GAS PROBE

(75) Inventors: Claes Nylander, Linköping (SE); Peter Hebo, Mjölby (SE); Fredrik Enquist, Linköping (SE)

(73) Assignee: Inficon AB, Linköping (SE)

( * ) Notice: Subject to any disclaimer, the term of this patent is extended or adjusted under 35 U.S.C. 154(b) by 590 days.

(21) Appl. No.: 12/991,212

(22) PCT Filed: May 5, 2008

(86) PCT No.: PCT/SE2008/050506
§ 371 (c)(1),
(2), (4) Date: Jan. 24, 2011

(87) PCT Pub. No.: WO2009/136821
PCT Pub. Date: Nov. 12, 2009

(65) Prior Publication Data
US 2011/0113860 A1    May 19, 2011

(51) Int. Cl.
*G01M 3/04* (2006.01)
*G01N 1/22* (2006.01)

(52) U.S. Cl.
USPC .......... 73/40.7; 73/863.57; 73/866.5; 73/45.5

(58) Field of Classification Search
USPC ............... 73/19.07, 31.05, 31.07, 40.7, 45.5, 73/863.57, 866.5
See application file for complete search history.

(56) References Cited

U.S. PATENT DOCUMENTS

| | | | | |
|---|---|---|---|---|
| 4,633,704 A | * | 1/1987 | Tantram et al. | 73/31.05 |
| 4,754,638 A | * | 7/1988 | Brayman et al. | 73/40.7 |
| 5,297,422 A | * | 3/1994 | Baret | 73/40.7 |
| 7,140,232 B2 | * | 11/2006 | Wright et al. | 73/25.01 |
| 2004/0154379 A1 | * | 8/2004 | Enquist et al. | 73/40.7 |
| 2004/0185554 A1 | * | 9/2004 | Daitch et al. | 435/309.1 |

(Continued)

FOREIGN PATENT DOCUMENTS

EP    0352371 A2    1/1990
WO    WO-2005/001410 A1    1/2005

OTHER PUBLICATIONS

PCT/ISA/210—International Search Report—Jan. 26, 2009.

(Continued)

*Primary Examiner* — Harshad R Patel
*Assistant Examiner* — Punam Roy
(74) *Attorney, Agent, or Firm* — Venable LLP; Eric J. Franklin

(57) ABSTRACT

A gas probe for sampling gas molecules from a fluid. A housing includes an orifice and is adapted to be arranged in gas communication with a test gas sensor. The probe includes a stack of layers, whereby gas sample molecules have to pass through all layers of the stack in order reach the sensor. The stack includes at least a first membrane layer, a first spacer layer, a first filter layer and a second spacer layer. The housing includes an inlet for introducing blocking gas molecules into the second spacer layer and an outlet for discharging blocking gas molecules out of the first spacer layer. The gas probe is connectable to a control unit for controlling the blocking gas flow into the second spacer layer.

13 Claims, 5 Drawing Sheets

(56) References Cited

U.S. PATENT DOCUMENTS

2006/0107774 A1* 5/2006 Meyberg ..................... 73/866.5
2008/0202210 A1   8/2008 Liepert
2010/0288020 A1* 11/2010 Enquist ......................... 73/40.7
2011/0290006 A1* 12/2011 Perkins et al. ................. 73/40.7

OTHER PUBLICATIONS

PCT/ISA/237—Written Opinion of the International Searching Authority—Jan. 26, 2009.

* cited by examiner

GAS PROBE FOR SAMPLING GAS MOLECULES FROM A FLUID AND A SYSTEM COMPRISING THE GAS PROBE

CROSS-REFERENCE TO RELATED APPLICATIONS

This application is the national phase of PCT/SE2008/050506 filed 5 May 2008.

TECHNICAL FIELD

The present invention relates to a gas probe for sampling gas molecules from a fluid. In addition, the present invention relates to a test gas detection system comprising the gas probe according to the invention and a leak testing system comprising the gas probe.

BACKGROUND OF THE INVENTION

There are many different applications in which it is necessary or desired to determine whether a fluid comprises a specific gas, i.e. a test gas, or not. In such applications it is common to perform sampling of gas molecules from the fluid by means of a gas probe and detect test gas molecules, if any, among the sampled gas molecules (i.e. gas sample molecules) by means of a test gas sensor. More specifically, gas sample molecules from the fluid are then allowed to enter into the interior of a gas probe housing through a gas probe orifice and test gas molecules, if any, among the gas sample molecules are detected by means of a test gas sensor arranged in gas communication with the interior of the gas probe housing. Furthermore, it might not only be necessary or desired to determine whether the test gas is present in the fluid or not, but also to measure the concentration thereof in the fluid. Then a measurement unit may be connected to the test gas sensor. The measurement unit interprets and measures signals from the sensor and provides, for example, a digital, electric, acoustic or optic signal corresponding to the concentration of the test gas molecules in a volume of gas sample molecules reaching the test gas sensor.

Leak testing is one application which may involve sampling of gas molecules from a fluid by means of a gas probe and detecting test gas molecules, if any, among the sampled gas molecules by means of a test gas sensor. In one leak testing approach, an object to be tested for leakage is pressurized with a tracer gas (the test gas is commonly denoted as tracer gas in leak testing), whereby tracer gas molecules pass through any leaks in the test object to the outside thereof. Gas molecules are then sampled external to the test object by means of a gas probe and tracer gas molecules, if any, among the sampled gas molecules are detected by means of a tracer gas sensor. In case tracer gas molecules are found among the sampled gas molecules, the test object comprises a leak. Furthermore, by measuring the tracer gas concentration in a volume of gas sample molecules reaching the tracer gas sensor by means of a measurement unit connected to the tracer gas sensor, the size of the leak may also be determined. Examples of commonly utilized tracer gases are helium, hydrogen, refrigerants, sulfur hexafluoride and carbon dioxide.

In another leak testing approach, the interior of a test object is evacuated and the tracer gas is sprayed onto the outside of the test object. Thereafter gas molecules are sampled from the interior of the test object by means of a gas probe and tracer gas molecules, if any, among the sampled gas molecules are detected by means of a tracer gas sensor.

The above described tracer gas methods may be applied for local leak testing, i.e. leak testing at a specific leakage testing point of the test object. When the above first described tracer gas method is applied for local leak testing, gas molecules are sampled at the specific leakage testing point external to the test object after pressurization of the test object with the tracer gas and tracer gas molecules, if any, among the sampled gas molecules are detected. When the other described tracer gas method is applied for local leak testing, the tracer gas is sprayed onto the test object at the specific leakage testing point. Thereafter gas molecules are sampled from the interior of the test object and tracer gas molecules, if any, among the sampled gas molecules are detected.

In addition, the above described tracer gas methods may be applied for so-called global leak testing, which also is called accumulation testing. In global leak testing, the test object is placed in a cabinet or test chamber, whereby it is tested whether the test object is leaking at any point or is leak tight, i.e. it is not tested whether there is a leak at a specific leakage testing point, but the "total" leakage of the test object is tested. When the above first described tracer gas method is applied for global leak testing, the test object is placed in a test chamber and pressurized with a tracer gas. Thereafter gas molecules are sampled from the volume in the test chamber outside the test object and tracer gas molecules, if any, among the sampled gas molecules are detected. When the other described tracer gas method is applied for global leak testing, the test object is placed in a test chamber and tracer gas is sprayed into the test chamber in order to surround the test object. Gas molecules are then sampled from the interior of the test object and tracer gas molecules, if any, among the sampled gas molecules are detected.

However, when a gas probe is utilized for sampling gas molecules from a fluid, different types of liquid and solid contaminants, such as e.g. dust, debris, oil and grease, may, together with the gas sample molecules, enter into the interior of the gas probe housing and further to a test gas sensor being arranged in gas communication with the interior of the gas probe housing. The test gas sensor and, thus, the measurements may be negatively affected by such contaminants. In addition, other components such as e.g. filters, hoses, tubes and valves arranged in gas communication with the interior of the gas probe housing may be negatively affected by such contaminants. For example, the life of such components may thereby be limited and the need for service and maintenance thereof may be increased. Thus, there is a need to protect the test gas sensor and any other components being arranged in gas communication with the interior of a probe housing from liquid and solid contaminants.

In addition, for different reasons it is also desired to be able to control the amount of test gas molecules reaching the test gas sensor. For example, some sensors have a limited measuring range in that they are saturated at high concentrations of test gas. Furthermore, some sensors are also harmed temporarily or permanently by high test gas concentrations. In addition, it is of course also desired to be able to switch off the sampling such that no test gas molecules reach the test gas sensor during certain periods.

WO 2005/001410 describes a leak detection system comprising a permeable member, which is arranged in gas communication with a tracer gas sensor. The permeable member is permeable to tracer gas (in this case helium) utilized in leak detection under specified conditions, but blocks other gases, liquids and particles. In one embodiment, the permeable member is made of quartz. The helium permeability of quartz varies with temperature, whereby the amount of tracer gas molecules reaching the sensor may be controlled by adjusting the temperature. At a relatively high temperature, helium permeability is high, whereas at a relatively low temperature, helium permeability is low, whereby sampling is switched off.

Thus, the permeable member disclosed in WO 2005/001410 could be arranged in a gas probe housing between the orifice and the test gas sensor in order to protect the test gas sensor and any other components being in gas communication with the interior of the gas probe housing from liquid and solid contaminants and to control the amount of test gas molecules reaching the test gas sensor (i.e. to protect the test gas sensor from saturation and over-exposure). However, a heating element is required in order to adjust the permeability of the permeable member, i.e. to achieve the control of the amount of test gas molecules reaching the sensor. In addition, the adjustment of the permeability of the permeable member is a relatively slow process, i.e. it takes a relatively long time to adjust the permeability and, thus, to adjust the amount of test gas molecules reaching the test gas sensor. Furthermore, the permeable member disclosed in WO 2005/001410 is mainly suited to be utilized when helium is the test gas and it is not suited to be utilized for applications on liquids, i.e. when gas molecules are to be sampled from a liquid in order to detect a specific test gas in the liquid.

Thus, there is still a need for an improved gas probe, which gas probe may be utilized for sampling gas molecules from a fluid, which gas probe comprises a probe housing with an orifice and which gas probe is adapted to be arranged such that the interior of the probe housing is arranged in gas communication with a test gas sensor, whereby the gas probe is improved such that a test gas sensor arranged in gas communication with the interior of the probe housing may be protected from liquid and solid contaminants as well as from over-exposure and saturation without the above mentioned drawbacks.

SUMMARY OF THE INVENTION

Accordingly, one object of the present invention is to provide an improved gas probe for sampling gas molecules from a fluid, said gas probe comprising a probe housing with an orifice for entrance of said gas sample molecules from said fluid into the interior of said probe housing, and said gas probe being adapted to be arranged such that said interior of said probe housing is arranged in gas communication with a test gas sensor configured to detect test gas molecules among said gas sample molecules.

A further object of the present invention is to provide an improved test gas detection system.

A still further object of the present invention is to provide an improved leak testing system.

Still other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures described herein.

BRIEF DESCRIPTION OF THE DRAWINGS

In the drawings, wherein like reference characters denote similar elements throughout the several views.

DETAILED DESCRIPTION OF PREFERRED EMBODIMENTS

The present invention provides a gas probe that may be utilized for sampling gas molecules from a fluid. As will be further described below, the gas probe may be utilized for sampling gas molecules from a fluid in order to determine whether a specific test gas is present in the fluid and to determine the concentration of the test gas in the fluid, respectively. The term "fluid" is herein intended to mean a substance, e.g. a liquid or a gas, that is capable of flowing and that changes its shape at a steady state when acted upon by a force tending to change its shape. The term "test gas" is herein intended to mean a specific gas, i.e. a specific gaseous substance or compound, whose presence, and possibly also concentration, in a fluid is/are to be determined. For example, the test gas may be a gas normally comprised in a fluid to be tested or a gas not normally comprised in a fluid to be tested. The term "measurement volume" is herein intended to mean a volume in which a fluid, from which sampling of gas molecules is to be performed, is comprised. For example, the measurement volume may be comprised in a closed test chamber, it may be the interior (or parts of the interior) of a test object, it may be a volume outside a test object, or any other volume comprising a fluid. In leak testing applications, a tracer gas may constitute the test gas. The term "tracer gas" is herein intended to mean a gas that is utilized to detect a leak of a test object, i.e. a gas that is to be detected after leak passage. The tracer gas may be a gas that is solely utilized for test purposes, i.e. a gas that is applied to the test object solely for the sake of detecting any leak, or a gas that is a normal component of an object to be tested for leakage. The term "blocking gas" is herein intended to denote a gas which is utilized in order to achieve a blocking gas flow that blocks or counteracts a gas sample flow. The blocking gas is a gas other than the test gas and is a gas for which the test gas sensor is non-sensitive. The term "test gas sensor" is herein intended to denote a device sensitive to the test gas.

Figure 1A:
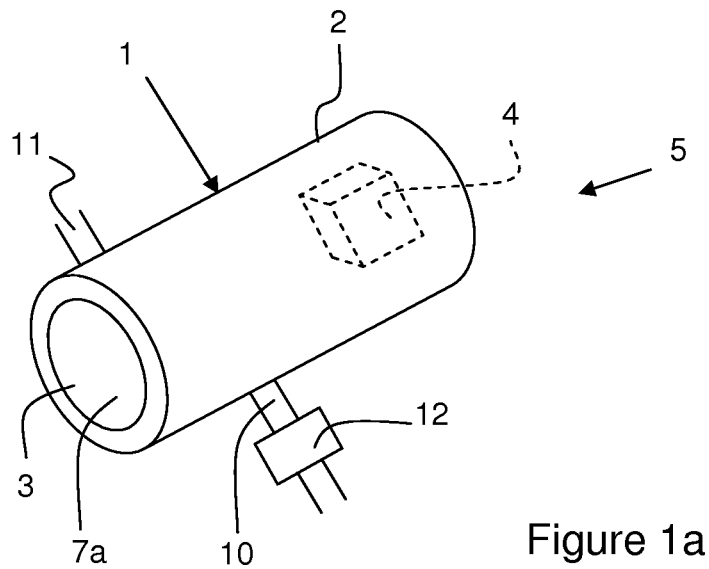
FIG. 1a shows a schematic perspective view of a first embodiment of a gas probe according to the invention.
Figure 1B:
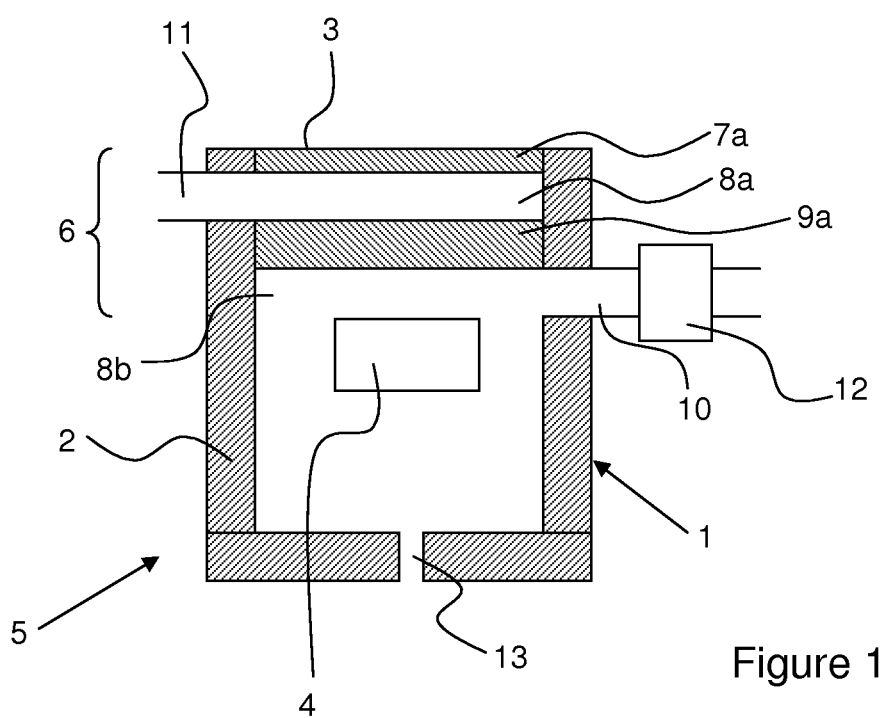
FIG. 1b shows a cross-sectional view of the first embodiment of the gas probe according to the invention.

FIG. 1a and 1b shows a schematic perspective view and a cross-sectional view, respectively, of a first embodiment of a gas probe 1 according to the invention, by which gas molecules may be sampled from a fluid. The gas probe 1 comprises a probe housing 2 with an orifice 3 for entrance of gas sample molecules from the fluid into the interior of the probe housing 2. Furthermore, the gas probe 1 is adapted to be arranged such that the interior of the probe housing 2 is arranged in gas communication with a test gas sensor 4. By the expression that "the gas probe is adapted to be arranged such that the interior of the probe housing is arranged in gas communication with a test gas sensor" is herein meant that the gas probe either is adapted such that a test gas sensor may be arranged in the interior of the probe housing or such that the interior of the probe housing is connectable to a separate unit comprising a test gas sensor. In the embodiment shown in FIGS. 1a and 1b, a test gas sensor 4 is arranged in the interior of the probe housing 2. Thus, the first embodiment of the gas probe 1 is adapted such that a test gas sensor 4 may be arranged in the interior of the probe housing 2, whereby the interior of the probe housing 2 is arranged in gas communication with the sensor 4. However, in other embodiments described below, a test gas sensor 4 is arranged in a separate sensor unit to which the interior of the probe housing 2 is connectable such that the interior of the probe housing 2 is arranged in gas communication with the sensor 4. According to the definition utilized herein, the test gas sensor 4 is not a part of the gas probe 1 according to the invention. Instead the gas probe 1 and the test gas sensor 4 are comprised in a test gas detection system 5 according to the invention.

The test gas sensor 4 is configured to selectively detect specific test gas molecules among sampled gas molecules, i.e. gas sample molecules. In the embodiment shown in FIGS. 1a and 1b, the test gas sensor may be a hydrogen gas sensitive sensor, an infrared gas analyzer or a semiconductor flammable gas sensor.

Furthermore, the gas probe 1 according to the invention comprises a protecting means 6. The protecting means 6 is constituted by a stack of layers. The stack 6 is arranged in the probe housing 2 such that it constitutes an obstacle in the flow path from the orifice 3 and further into the probe housing 2 for gas sample molecules from the fluid. The gas sample molecules have to pass the obstacle in order to pass further into the probe housing 2. More specifically, the stack 6 is arranged in the probe housing 2 in the flow path from the orifice 3 and further into the probe housing 2 for gas sample molecules from the fluid such that gas sample molecules from the fluid are required to pass through all layers of the stack 6 in order to pass further into the probe housing 2, i.e. gas sample molecules from the fluid can not pass the stack 6 on sides thereof. In the first embodiment shown in FIGS. 1a and 1b, the stack 6 is arranged in the probe housing 2 such that the edges of each layer of the stack 6 are arranged connected with walls of the probe housing 2 such that gas sample molecules can not pass between the stack 6 and any wall of the probe housing 2.

Furthermore, the stack 6 is arranged in the probe housing 2 such that gas sample molecules from the fluid are required to pass through all layers of the stack 6 in order to reach the test gas sensor 4, i.e. the stack 6 is positioned between the orifice 3 and the test gas sensor 4. The gas sample molecules pass through the stack 6 in a gas sample flow, i.e. in a flow being directed from the orifice 3 towards the test gas sensor 4. According to the invention, each layer of the stack 6 is selected from the group consisting of: a membrane layer, a filter layer and a spacer layer.

In the first embodiment of the gas probe 1 shown in FIGS. 1a and 1b, the stack 6 comprises, seen in the gas sample flow direction, a first membrane layer 7a, a first spacer layer 8a, a first filter layer 9a and a second spacer layer 8b. Thus, the first membrane layer 7a is the outermost layer of the stack 6 and the second spacer layer 8b is the innermost layer of the stack 6.

The term "membrane layer" is herein intended to denote a layer constituted by a membrane. A "membrane" according to the invention is a porous separating member, which is permeable to the test gas and possibly also to one or more other gases. However, a "membrane" according to the invention blocks completely, or at least essentially, penetration of contaminants in the form of liquid or solid particles. Thus, it blocks penetration of e.g. dust, debris, oil and grease. Furthermore, the dimension of the pores of a membrane according to the invention is such that test gas molecules may penetrate the membrane by means of essentially molecular flow (which also is denoted as "diffusion") only, i.e. a flow of test gas molecules through a membrane is mainly molecular (essentially not laminar). Consequently, a "membrane" according to the invention may also be denoted as a diffusion barrier.

Furthermore, the dimension of the pores of the membrane may be such that the membrane is gas selective, i.e. it may be permeable to test gas molecules, but at least essentially impermeable to certain other gases or all other gases. For example, it may be permeable to test gas molecules, but at least essentially permeable to gas molecules of higher molecular mass. Thus, it may be permeable to the test gas while substantially blocking heavier gases. Alternatively, it may be impermeable to test gas molecules only. Furthermore, it may be impermeable to the blocking gas. A "membrane" according to the invention may be a member selected from the group consisting of: a member of a woven polymer material, a member of a nonwoven material and a member of a porous material. For example, a "membrane" according to the invention may be of polytetrafluoroethylene such as e.g. Teflon®.

The term "molecular flow" (or "diffusion") is herein intended to denote a flow in which a gaseous molecule predominantly collides with a structure in the flow path (e.g. a wall of a pore in a membrane) instead of with another gaseous molecule. The essential feature of molecular flow according to the invention is the fact that the flow of test gas is driven by partial pressure difference only and that test gas therefore can flow in case of no or even against negative total pressure difference.

The term "laminar flow" is herein intended to denote a flow in which a gaseous molecule predominantly collides with another gaseous molecule instead of with a structure in the flow path. The essential feature of laminar flow according to the invention is that it is viscous and thereby inhibits or restricts molecular flow (diffusion) in a direction opposite to the laminar flow.

The term "filter layer" is herein intended to denote a layer constituted by a filter. A "filter" according to the invention is a porous member. More specifically, the dimension of the pores is such that test gas molecules as well as blocking gas molecules may penetrate the filter by means of laminar flow, i.e. a flow of test gas molecules or blocking gas molecules through a filter is mainly laminar (essentially not molecular). Thus, a "filter" according to the invention is a member, which is permeable to at least the test gas and the blocking gas and has pores of a greater dimension than a membrane according to the invention. As will be further described below a "filter layer" according to the invention may also be denoted as a "distributing layer". A "filter" according to the invention may be a member selected from the group consisting of: a sintered filter, a member of a woven metal material, a member of a woven polymer material, a member of a nonwoven material and a member of a porous material.

The term "spacer layer" is herein intended to denote a layer constituted by a spacer. A "spacer" according to the invention may be a member that has greater pores than a filter according to the invention. Alternatively, a "spacer" according to the invention may be void space. Test gas molecules and blocking gas molecules may pass through a "spacer" by means of laminar flow, i.e. a flow of test gas molecules or blocking gas molecules through a spacer is mainly laminar (essentially not molecular). A "spacer" according to the invention may be a member selected from the group consisting of: void space, a sintered filter, a member of a woven metal material, a member of a woven polymer material, a member of a nonwoven material and a member of a porous material. Thus, each spacer layer of the stack 6 may be respectively constituted by a member selected from this group.

In accordance with the above definitions, a membrane has a higher flow resistance for test gas molecules than a filter and a filter has a higher flow resistance for test gas molecules than a spacer. Likewise, a membrane has a higher flow resistance for blocking gas molecules than a filter and a filter has a higher flow resistance for blocking gas molecules than a spacer.

In accordance with the above, the test gas may pass through all layers of the stack 6 to the test gas sensor 4. Thus, gas sample molecules from the fluid which are test gas molecules may pass through all layers of the stack 6. However, whether gas sample molecules from the fluid being of another gas than the test gas may pass through the stack 6 depends on the type of the membrane of the membrane layer 7*a*. Thus, in case the membrane permits test gas molecules to pass through only, all gas sample molecules reaching the test gas sensor 4 are test gas molecules. However, in case the membrane permits other gas molecules to pass through too, gas sample molecules reaching the test gas sensor may be test gas molecules or gas molecules of other gases permitted to penetrate the membrane of the first membrane layer 7*a*.

Membranes, filters and spacers having the above characteristics are commercially available and may be selected by a person skilled in the art in order to suit a particular application. In particular, they are selected depending on the test gas of a particular application, i.e. depending on the specific gas whose presence is to be detected in a fluid in a particular application.

In the first embodiment shown in FIGS. 1*a* and 1*b*, the protecting means 6 is shown as being positioned at the orifice 3. More specifically, in FIGS. 1*a* and 1*b* the protecting means 6 is positioned such that one layer, i.e. the first membrane layer 7*a*, is positioned in the orifice 3. It may then be seen as constituting the orifice 3. However, in alternatives (not shown) the protecting means 6 may be arranged at another position in the probe housing 2, i.e. at a distance from the orifice 3.

Furthermore, the probe housing 2 comprises an inlet 10 for introducing a blocking gas, i.e. blocking gas molecules, into the second spacer layer 8*b* from the outside of the probe housing 2 and an outlet 11 for discharging the blocking gas molecules out of the first spacer layer 8*a* to the outside of the probe housing 2. In accordance with the above definitions, the first filter layer 9*a* is permeable to the blocking gas molecules. In order to reach the outlet 11, the blocking gas molecules are required to pass through the first filter layer 9*a* in a blocking gas flow being directed in a direction opposite to the direction of the gas sample flow. Thus, a blocking gas flow is in the first filter layer 9*a* directed from the second spacer layer 8*b* towards the first spacer layer 8*a*. For example, the blocking gas may be nitrogen gas or air.

As above described, the first filter layer 9*a* has a higher flow resistance for the blocking gas than the second spacer layer 8*b*. More specifically, the first filter layer 9*a* has such a flow resistance for the blocking gas compared to the second spacer layer 8*b* that it works as a flow distributing layer. Thus, it is arranged in order to distribute a flow of blocking gas introduced into the second spacer layer 8*b* via the inlet 10 more evenly over the first filter layer 9*a*, i.e. more evenly over the surface of the first filter layer 9*a* arranged adjacent to the second spacer layer 8*b*. Preferably, the first filter layer 9*a* has such a flow resistance for the blocking gas compared to the second spacer layer 8*b* such that a flow of blocking gas introduced into the second spacer layer 8*b* is distributed such that a blocking gas flow over the complete, or at least essentially the complete, first filter layer 9*a* is achieved in a direction towards the first spacer layer 8*a*.

Since an achieved blocking gas flow through the first filter layer 9*a* is directed in a direction opposite to the direction of a gas sample flow, it counteracts a flow of gas sample molecules there through. The degree of counteraction depends on, inter alia, the magnitude of the achieved blocking gas flow through the first filter layer 9*a*, which in turn depends on, inter alia, the magnitude of the blocking gas flow introduced into the second spacer layer 8*b*. In order to enable control of the magnitude of the blocking gas flow introduced into the second spacer layer 8*b* and, thus, the above mentioned counteraction, the gas probe 1 according to the invention is connectable to a control unit 12. The control unit 12 is arranged for controlling the flow of blocking gas molecules introduced into the second spacer layer 8*b* through the inlet 10 so as to control the blocking gas flow through the first filter layer 9*a* in order to control the opposite gas sample flow through the first filter layer 9*a*. For example, the control unit 12 may be valve or a controllable speed pump.

FIGS. 1*a* and 1*b* show the first embodiment of the gas probe 1 as being connected to a control unit 12. The gas probe 1 according to the invention may comprise the control unit 12. Alternatively, however, the gas probe 1 does not comprise the control unit 12, but is connectable to the control unit 12.

Thus, according to the invention it is possible to control the flow of gas sample molecules, i.e. the amount of gas sample molecules, passing through the first filter layer 9*a* by controlling the magnitude of the blocking gas flow introduced into the second spacer layer 8*b*. Since gas sample molecules are required to pass through the first filter layer 9*a* in order to reach the test gas sensor 4, the amount of gas sample molecules reaching the test gas sensor 4 may thereby also be controlled. The magnitude of the blocking gas flow may be controlled such that no, or essentially no, gas sample molecules manage to pass through the first filter layer 9*a*, i.e. such that the gas sample flow through the first filter layer 9*a* is completely blocked or substantially counteracted. Then the sampling is completely or substantially shut-off. Thus, by means of controlling the magnitude of the blocking gas flow passing through the first filter layer 9*a*, the sampling may be switched on and off. Alternatively, the magnitude of the blocking gas flow may be controlled such that a certain amount of gas sample molecules is permitted to pass through the first filter layer 9*a*, i.e. such that the gas sample flow through the first filter layer 9*a* is counteracted to a certain degree only. When a gas sample flow is counteracted to a certain degree only, gas sample molecules may pass through the first filter layer 9*a* against the blocking gas flow there through. This may be utilized in order to protect the test gas sensor 4 from saturation and/or over-exposure, i.e. exposure to such high concentrations of test gas that the sensor 4 is harmed. In addition, the blocking gas flow may be completely shut-off.

Furthermore, by the possibility to control the magnitude of the blocking gas flow, it is also possible to set the rejection rate of the gas probe 1. Then a magnitude of the blocking gas flow is set which means that all concentrations of test gas molecules below a certain limit do not reach the test gas sensor 4, i.e. concentrations of test gas molecules below the limit are then rejected.

Furthermore, the first embodiment of the gas probe 1 shown in FIG. 1*a* is schematically shown as having a cylindrical shape. However, it may have any suitable shape, such as e.g. a gun-like shape.

In addition, the gas probe 1 according to the invention may be arranged to be connected to other components in a test gas detection system and may therefore comprise one or more means for connection to other components. One connection means is schematically shown in FIG. 1*b* and denoted by 13.

In other embodiments, the stack 6 of the gas probe 1 according to the invention may comprise one or more further membrane layers and/or one or more further filter layers and/or one or more further spacer layers compared to the first embodiment. Thus, the stack 6 may comprise any suitable number of membrane layers, filter layers and spacer layers. However, in all embodiments the stack 6 comprises, seen in the gas sample flow direction, the first membrane layer 7*a*, the first spacer layer 8*a*, the first filter layer 9*a* and the second spacer layer 8*b*.

Figure 2:
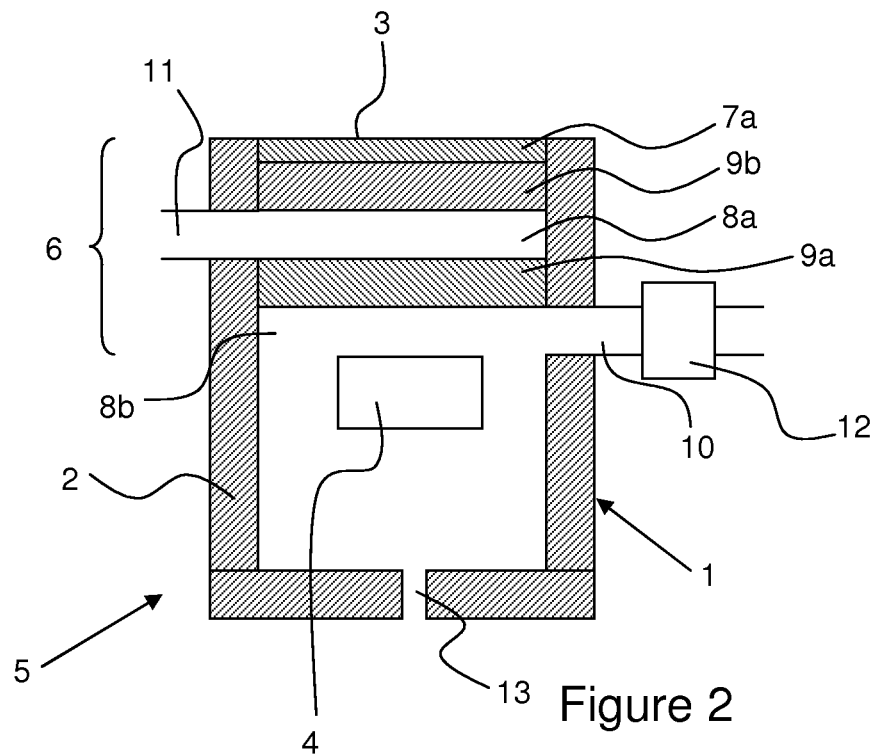
FIG. 2 shows a second embodiment of the gas probe according to the invention.
Figure 3:
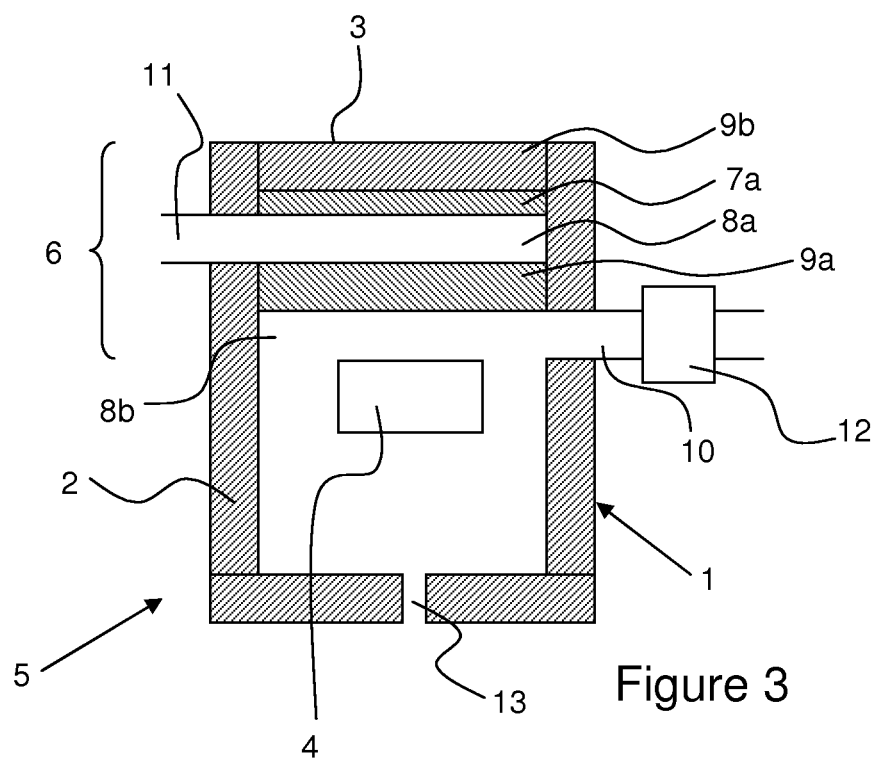
FIG. 3 shows a third embodiment of the gas probe according to the invention.

FIGS. 2 and 3 show a second and a third embodiment of the gas probe 1 according to the invention. The second and third embodiments correspond to the first embodiment except for concerning the fact that the stack 6 further comprises a second filter layer 9*b* arranged adjacent to the first membrane layer 7*a*. In the second embodiment shown in FIG. 2, the second filter layer 9*b* is interposed between the first membrane layer 7*a* and the first spacer layer 8*a*, whereby the second filter layer 9*b* is arranged after the first membrane layer 7*a*, but before the first spacer layer 8*a*, seen in the direction of the gas sample flow through the stack 6. In the third embodiment shown in FIG. 3, the second filter layer 9*b* is arranged before the first membrane layer 7*a* seen in the direction of the gas sample flow through the stack 6. The second filter layer 9*b* constitutes a mechanical support as well as a protecting device for the first membrane layer 7*a*.

Figure 4A:
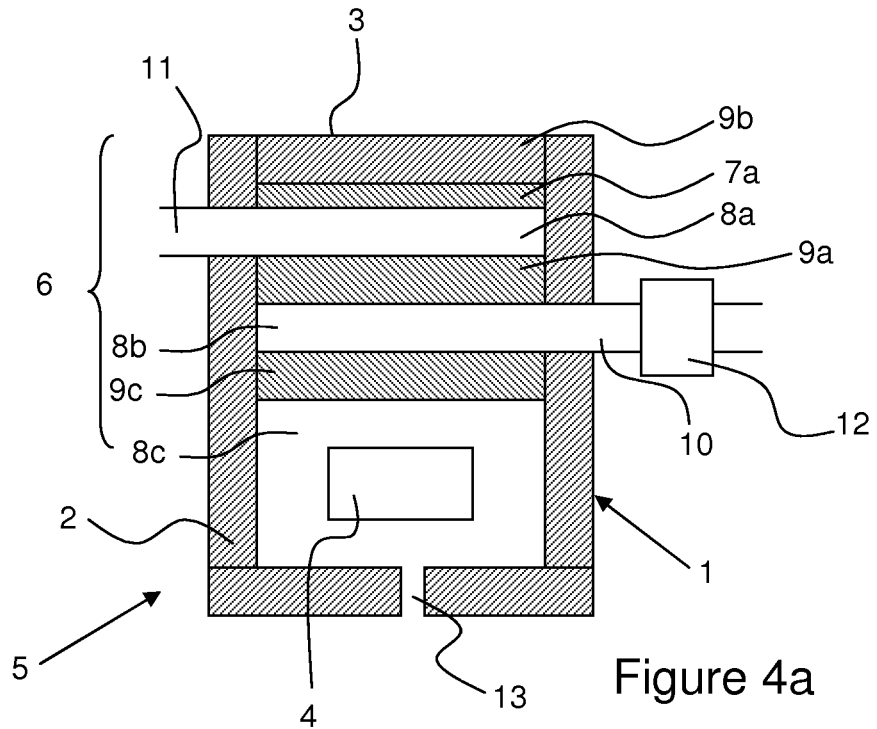
FIG. 4a shows a variant of the third embodiment of the gas probe according to the invention.

Furthermore, any of the first, second and third embodiments shown in FIGS. 1*a*, 1*b*, 2 and 3 may be varied such that it further comprises a third filter layer 9*c* arranged after the second spacer layer 8*b* seen in the direction of the gas sample flow through the stack 6 and a third spacer layer 8*c* arranged after the third filter layer 9*c* seen in the direction of the gas sample flow through the stack 6. One such variant is shown in FIG. 4*a*. More specifically, the variant shown in FIG. 4*a* corresponds to the third embodiment except for concerning the fact that it further comprises a third filter layer 9*c* arranged after the second spacer layer 8*b* seen in the direction of the gas sample flow through the stack 6 and a third spacer layer 8*c* arranged after the third filter layer 9*c* seen in the direction of the gas sample flow through the stack 6. Corresponding variants of the first and second embodiments are not shown. The third filter layer 9*c* may be arranged in order to protect the sensor 4 from pressure impulses and temperature shocks arising due to the control of the flow of the blocking gas (i.e. when the blocking gas flow is turned on and off).

Figure 4B:
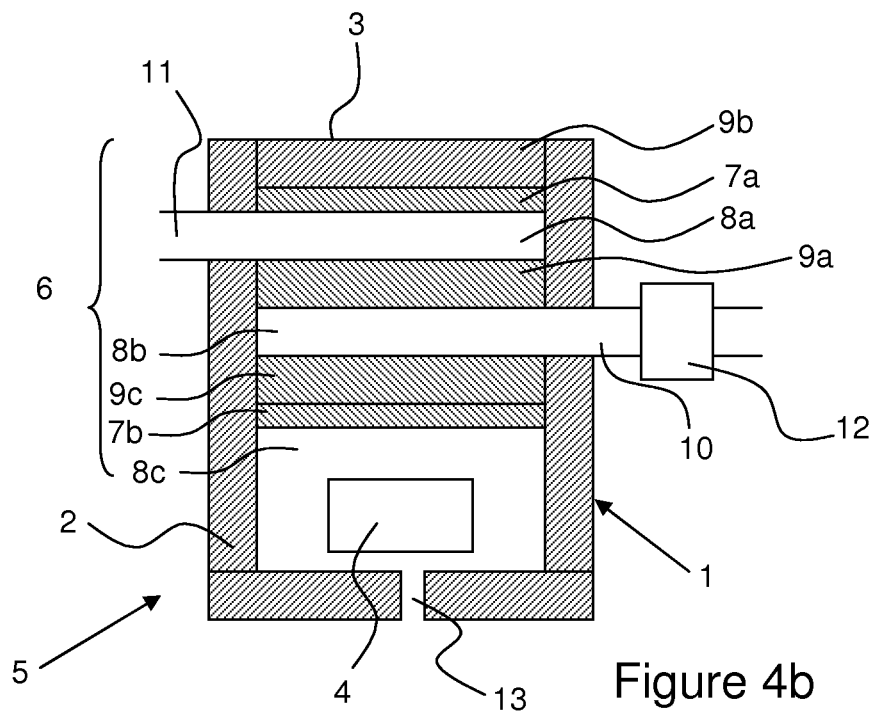
FIG. 4b shows a further variant of the third embodiment of the gas probe according to the invention.

Any of the variants in which the stack 6 comprises a third filter layer 9*c* arranged after the second spacer layer 8*b* seen in the direction of the gas sample flow through the stack 6 and a third spacer layer 8*c* arranged after the third filter layer 9*c* seen in the direction of the gas sample flow through the stack 6, may optionally further comprise a second membrane layer 7*b* interposed between the third filter layer 9*c* and the third spacer layer 8*c*. FIG. 4*b* shows one such variant, which corresponds to the variant shown in FIG. 4*a* except for concerning the fact that it further comprises the second membrane layer 7*b*. The second membrane layer 7*b* may also be arranged in order to protect the sensor 4 from pressure impulses and temperature shocks arising due to the control of the flow of the blocking gas (i.e. when the blocking gas flow is turned on and off).

Figure 5:
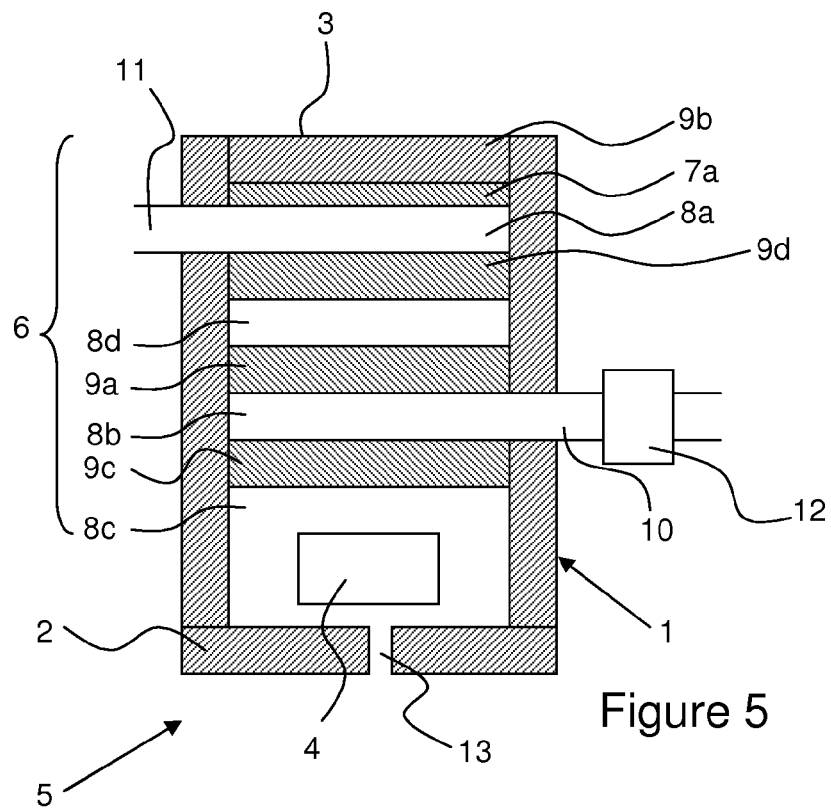
FIG. 5 shows still a further variant of the third embodiment of the gas probe according to the invention.

Furthermore, any of the above described embodiments or variants thereof may be further varied such that the stack 6 comprises a fourth filter layer 9*d* and a fourth spacer layer 8*d* interposed between the first spacer layer 8*a* and the first filter layer 9*a*. The fourth filter layer 9*d* is then arranged before the fourth spacer layer 8*d* seen in the direction of the gas sample flow through the stack 6. FIG. 5 shows one such variant, which corresponds to the variant shown in FIG. 4*a* except for concerning the fact that it further comprises the fourth filter layer 9*d* and the fourth spacer layer 8*d* interposed between the first spacer layer 8*a* and the first filter layer 9*a*. The fourth filter layer 9*d* has a higher flow resistance for the blocking gas than the fourth spacer layer 8*d*, i.e. it works, just as the first filter layer 9*a*, as a flow distributing layer. The fourth filter layer 9*d* may be arranged in order to achieve an improved distribution of the blocking gas flow introduced through the inlet 10.

In embodiments comprising the fourth filter layer 9*d* and the fourth spacer layer 8*d*, a blocking gas flow is achieved that is directed from the second spacer layer 8*b* to the first spacer layer 8*a* through both the first filter layer 9*a* and the fourth filter layer 9*d*. Thereby, the blocking gas flow counteracts the gas sample flow through both the first filter layer 9*a* and the fourth filter layer 9*d*.

As mentioned above, the stack 6 of the gas probe 1 according to the invention may comprise any suitable number of membrane layers, filter layers and spacer layers. The respective membrane of the membrane layer(s), the respective filter of the filter layer(s) and the respective spacer of the spacer layer(s) may be individually selected from the above mentioned membrane members, filter members and spacer members, respectively. Thus, any two membrane layers may be of the same type or different types, i.e. they may have the same or different characteristics. The same applies to any two filter layers and any two spacer layers. In the figures, the spacer layer(s) are shown as being void space. However, according to the above the spacer of the spacer layer(s) need not be void space, but may be selected form the above mentioned group.

When a sample of gas molecules is to be drawn from a liquid, it is especially suitable to utilize the second embodiment of the gas probe 1 or any variants thereof. This is due to the fact that the first membrane layer 7*a* then may have to be put in contact with the liquid.

In use of any of the above described embodiments of the gas probe 1 according to the invention, gas molecules are sampled from a fluid. Then gas sample molecules from the fluid enter into the interior of the probe housing 2 through the orifice 3. However, the stack 6 is positioned in the gas probe housing 2 such that gas sample molecules have to pass through the stack 6 in order to pass further into the probe housing 2 and reach the sensor 4. The first membrane layer 7*a* of the stack 6 decides which gas molecules may pass further into the gas probe housing 2 from the fluid, i.e. the first membrane layer 7*a* decides which types of gas molecules that may be found among the gas sample molecules that pass further into the probe housing 2. Depending on the characteristics of the first membrane layer 7*a* exclusively test gas molecules may penetrate the first membrane layer 7*a* or test gas molecules as well as other gas molecules may penetrate the first membrane layer 7*a*. In addition, the first membrane layer 7*a* blocks penetration of liquid and solid contaminants, whereby the sensor 4 as well as any other components being in gas communication with the interior of the probe housing 2 are protected from liquid and solid contaminants. A blocking gas flow may be introduced into the second spacer layer 8b through the inlet 10 in order to achieve a blocking gas flow through at least the first filter layer 9a, which is directed in a direction opposite to the direction of the gas sample flow there through. By means of a control unit 12 connected to the gas probe 1, the magnitude of the blocking gas flow may be controlled. Thereby the amount of gas sample molecules and, thus, test gas molecules, passing through the first filter layer 9a and, thus, reaching the test gas sensor 4 may be controlled, whereby the sensor 4 may be protected from saturation and from being exposed to such high amounts of test gas molecules that it is harmed. In addition, sampling may be switched on and off by controlling the blocking gas flow.

The gas probe 1 according to the invention may be utilized in many different applications in which it is necessary or desired to detect test gas molecules in a fluid. For example, it may be utilized in a leak testing application such as e.g. any of the above described leak testing methods in which a tracer gas is utilized. Then the tracer gas constitutes the test gas. The gas probe 1 is then utilized for sampling gas molecules from a fluid and tracer gas molecules, if any, in the fluid is sensed by means of the sensor 4, which selectively detects the tracer gas. The tracer gas may be selected from the group consisting of: hydrogen, helium, carbon dioxide, sulphur hexafluoride, and a hydrocarbon.

Figure 6:
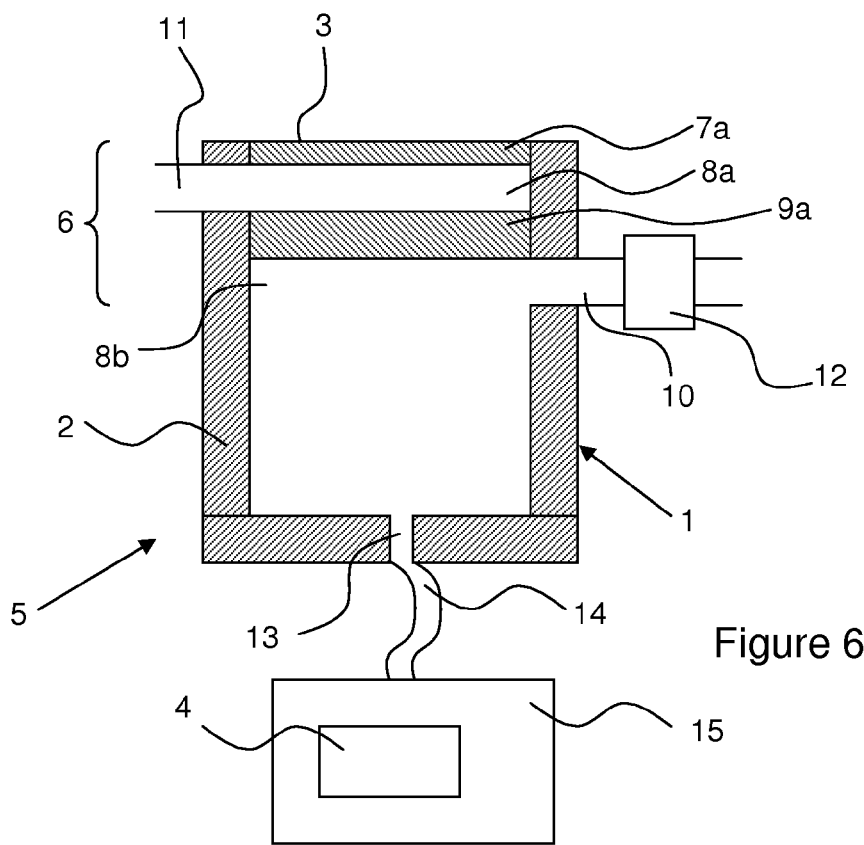
FIG. 6 shows one embodiment of a test gas detection system according to the invention.

In the embodiments of the gas probe 1 and variants thereof described above, the gas probe 1 is adapted such that the test gas sensor 4 may be arranged in the probe housing 2. However, any of the embodiments of the gas probe 1 and variants thereof described above may be varied such that the gas probe 1 is adapted such that the test gas sensor 4 instead is comprised in a separate unit to which the interior of the probe housing 2 is connectable. In such embodiments, the sensor 4 may be, for example, a hydrogen gas sensitive sensor, an infrared gas analyzer, a semiconductor flammable gas sensor or a mass spectrometer. FIG. 6 shows the first embodiment of the gas probe 1 in cross-section connected to a separate sensor unit 15 comprising the test gas sensor 4. The gas probe 1 is connected to the sensor unit 15 via the connection means 13 and a hose 14.

Figure 7:
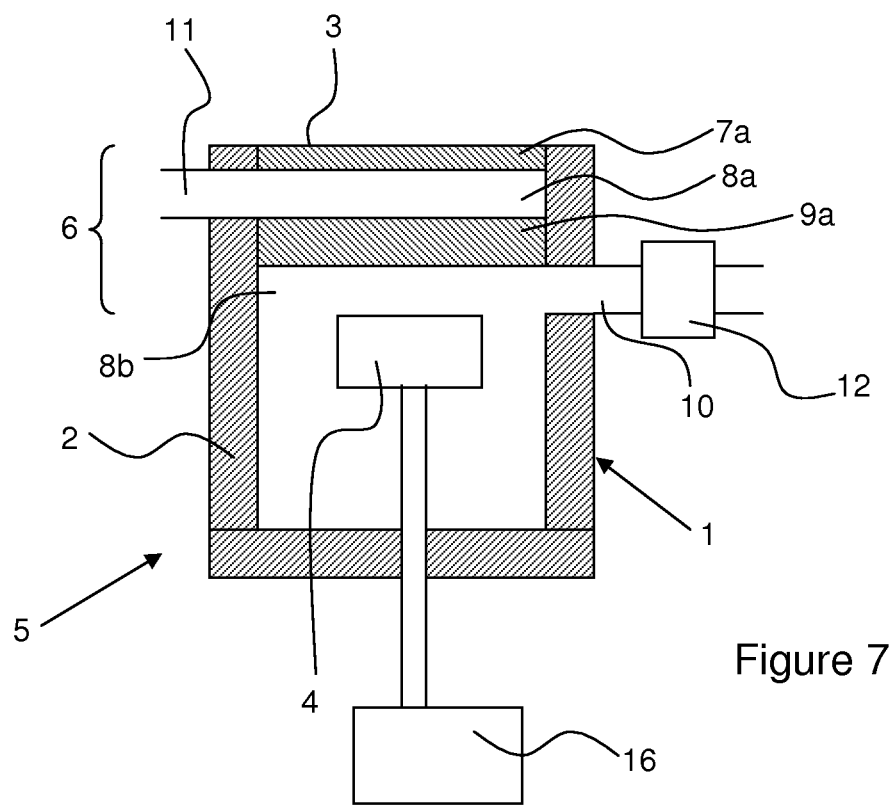
FIG. 7 shows a test gas detection system comprising a measurement unit according to the invention.

The present invention relates also to a test gas detection system 5, which comprises any of the above embodiments of the gas probe 1, or variants or alternatives thereof, and the test gas sensor 4. The test gas sensor 4 may be comprised in the interior of the probe housing 2 (as shown in FIGS. 1a, 1b, 2, 3, 4a, 4b and 5) or in a separate sensor unit 15 (FIG. 6). The test gas detection system 5 according to the invention may optionally further comprise at least one device selected from the group consisting of: a blocking gas source (not shown), a blocking gas pump (not shown) and a measurement unit (FIG. 7). The blocking gas source is arranged to constitute a source of blocking gas and the blocking gas pump is arranged to constitute a pump for pumping blocking gas from the blocking gas source to the inlet 10. A test gas detection system 5 in which the sensor 4 is comprised in a separate sensor unit 15 may optionally also comprise a suction flow generating device (not shown), by which a suction flow of gas molecules may be generated from the interior of the probe housing 2 to the sensor unit 15. The suction flow is generated in order to accelerate transportation of gas sample molecules that have passed through the stack 6 to the sensor 4. FIG. 6 shows one example of a test gas detection system 5 according to the invention in which the sensor 4 is comprised in a separate sensor unit 15.

As mentioned above, a test gas detection system 5 according to the invention may optionally further comprise a measurement unit. The measurement unit 16 is arranged to interpret and measure signals from the sensor 4 and provides, for example, a digital, electric, acoustic or optic signal corresponding to the concentration of test gas molecules in a volume of gas sample molecules reaching the test gas sensor 4. One example of a test gas detection system 5 comprising a measurement unit 16 is shown in FIG. 7, whereby the system 5 comprises the first embodiment of the gas probe 1.

In addition, the present invention relates also to a leak testing system, which comprises a test gas detection system 5 according to the invention and at least one device selected from the group consisting of: a sealable test chamber arranged to receive a test object, a flange for connection of the gas probe to the test chamber, a tracer gas source, a tracer gas control unit, a tracer gas pressure regulator, a vacuum pump, a fixture for the test object, and a fixture control unit. The test chamber may be a chamber utilized in accumulation testing. The tracer gas source is arranged to constitute a source of tracer gas. The tracer gas control unit administrates the filling of tracer gas from the tracer gas source into the test object to be tested or into an enclosure surrounding the test object. The tracer gas pressure regulator is arranged to control the output pressure from the tracer gas source. The fixture for a test object is arranged to connect to a test object for filling and removing of gas as well as to seal any other openings not constituting leak openings. The fixture control unit is arranged to manoeuvre the connections and seals of the fixture.

Furthermore, in case the gas probe 1 according to the invention is utilized in one of the above mentioned accumulation testing methods, whereby an object to be tested for leakage is positioned in a closed chamber and the test object is pressurized with a tracer gas, the gas probe 1 is positioned in leak-tight connection with the chamber. More specifically, the orifice 3 of the gas probe 1 is positioned in leak-tight connection with the chamber. The chamber is arranged to collect any tracer gas escaping from the test object.

At one or more points in the test cycle, gas molecules are sampled from the volume in the chamber outside the test object by means of the gas probe 1.

By means of the gas probe 1 according to the invention, it is possible to perform sampling of gas molecules from the fluid in the chamber without essentially reducing the pressure within the chamber. This is due to the fact that gas sample molecules are required to pass through the first membrane layer 7a by diffusion, i.e. concentration differences is the reason for why gas sample molecules pass from the chamber and into the gas probe 1. Thereby, only molecules of gases whose concentration differ between the chamber and the gas probe 1 will pass into the gas probe 1. For example, air is usually comprised both in the chamber and in the gas probe, whereby air is at least essentially not passed from the chamber and into the gas probe 1 during sampling. Thereby, a certain volume of air is not removed from the chamber during each sampling (as is the case in many prior art devices). In case a certain volume of air would be removed from the chamber during each sampling, the pressure in the chamber would be reduced for each sampling. The measurement results would then be negatively affected because one sampling would affect the results of a subsequent sampling. Since the gas probe 1 according to the invention does not remove a certain volume of gas from the chamber during each sampling, the gas probe 1 according to the invention may be utilized for detecting leaks more accurately, more reliably and with more sensitivity.

Thus, while there have been shown and described and pointed out fundamental novel features of the invention as applied to preferred embodiments thereof, it will be understood that various omissions and substitutions and changes in the form and details of the devices, method steps and products illustrated may be made by those skilled in the art. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas probe for sampling gas molecules from a fluid, said gas probe comprising;
   a probe housing with an orifice for entrance of said gas sample molecules from said fluid into an interior of said probe housing, and said gas probe being adapted to be arranged such that said interior of said probe housing is arranged in gas communication with a test gas sensor configured to detect test gas molecules among said gas sample molecules,
   a protecting member comprising a stack of layers, whereby said stack is arranged in said probe housing in a flow path for gas sample molecules from said orifice and further into said probe housing such that gas sample molecules are required to pass through all layers of said stack in order to pass further into said probe housing and in order to reach said test gas sensor, whereby gas sample molecules pass through said stack in a gas sample flow, and whereby said stack comprises, seen in a direction of said gas sample flow through said stack, at least a first membrane layer, a first spacer layer, a first filter layer and a second spacer layer,
   wherein said probe housing comprises an inlet for introducing blocking gas molecules into said second spacer layer and an outlet for discharging blocking gas molecules out of said first spacer layer, whereby said blocking gas molecules are required to pass through said first filter layer in a blocking gas flow being directed in a direction opposite to the direction of said gas sample flow in order to reach said outlet, and
   wherein said gas probe is connectable to a control unit for controlling the flow of blocking gas molecules into said second spacer layer through said inlet so as to control said blocking gas flow through said first filter layer in order to control said gas sample flow through said first filter layer.

2. The gas probe according to claim 1, wherein said gas probe comprises said control unit.

3. The gas probe according to claim 1, wherein said stack further comprises a second filter layer interposed between said first membrane layer and said first spacer layer, whereby said second filter layer is arranged after said first membrane layer but before said first spacer layer seen in the direction of said gas sample flow through said stack.

4. The gas probe according to claim 1, wherein said stack further comprises a second filter layer arranged before said first membrane layer seen in the direction of said gas sample flow through said stack.

5. The gas probe according to claim 1, wherein said stack further comprises a third filter layer arranged after said second spacer layer seen in the direction of said gas sample flow through said stack and a third spacer layer arranged after said third filter layer seen in the direction of said gas sample flow through said stack.

6. The gas probe according to claim 5, wherein said stack further comprises a second membrane layer interposed between said third filter layer and said third spacer layer.

7. The gas probe according to claim 1, wherein said stack further comprises a fourth filter layer and a fourth spacer layer interposed between said first spacer layer and said first filter layer, whereby said fourth filter layer is arranged before said fourth spacer layer seen in the direction of said gas sample flow through said stack.

8. The gas probe according to claim 1, wherein said test gas is selected from the group consisting of: hydrogen, helium, carbon dioxide, sulphur hexafluoride, and a hydrocarbon.

9. A test gas detection system, comprising:
   a gas probe comprising a probe housing with an orifice for entrance of said gas sample molecules from said fluid into an interior of said probe housing, and said gas probe being adapted to be arranged such that said interior of said probe housing is arranged in gas communication with a test gas sensor configured to detect test gas molecules among said gas sample molecules; a protecting member comprising a stack of layers, whereby said stack is arranged in said probe housing in a flow path for gas sample molecules from said orifice and further into said probe housing such that gas sample molecules are required to pass through all layers of said stack in order to pass further into said probe housing and in order to reach said test gas sensor, whereby gas sample molecules pass through said stack in a gas sample flow, and whereby said stack comprises, seen in a direction of said gas sample flow through said stack, at least a first membrane layer, a first spacer layer, a first filter layer and a second spacer layer; wherein said probe housing comprises an inlet for introducing blocking gas molecules into said second spacer layer and an outlet for discharging blocking gas molecules out of said first spacer layer, whereby said blocking gas molecules are required to pass through said first filter layer in a blocking gas flow being directed in a direction opposite to the direction of said gas sample flow in order to reach said outlet; and wherein said gas probe is connectable to a control unit for controlling the flow of blocking gas molecules into said second spacer layer through said inlet so as to control said blocking gas flow through said first filter layer in order to control said gas sample flow through said first filter layer; and
   a test gas sensor.

10. The test gas detection system according to claim 9, wherein said test gas sensor is arranged in the interior of said probe housing of said gas probe.

11. The test gas detection system according to claim 9, wherein said test gas sensor is arranged in a separate sensor unit being connectable to the interior of said probe housing of said gas probe.

12. The test gas detection system according to claim 9, further comprising:
   at least one device selected from the group consisting of: a blocking gas source, a blocking gas pump and a measurement unit.

13. A leak testing system, comprising:
   a test gas detection system a gas probe comprising a probe housing with an orifice for entrance of said gas sample molecules from said fluid into an interior of said probe housing, and said gas probe being adapted to be arranged such that said interior of said probe housing is arranged in gas communication with a test gas sensor configured to detect test gas molecules among said gas sample molecules; a protecting member comprising a stack of layers, whereby said stack is arranged in said probe housing in a flow path for gas sample molecules from said orifice and further into said probe housing such that gas sample molecules are required to pass through all layers of said stack in order to pass further into said probe housing and in order to reach said test gas sensor, whereby gas sample molecules pass through said stack in a gas sample flow, and whereby said stack comprises, seen in a direction of said gas sample flow through said stack, at least a first membrane layer, a first spacer layer, a first filter layer and a second spacer layer; wherein said probe housing comprises an inlet for introducing blocking gas molecules into said second spacer layer and an outlet for discharging blocking gas molecules out of said first spacer layer, whereby said blocking gas molecules are required to pass through said first filter layer in a blocking gas flow being directed in a direction opposite to the direction of said gas sample flow in order to reach said outlet; and wherein said gas probe is connectable to a control unit for controlling the flow of blocking gas molecules into said second spacer layer through said inlet so as to control said blocking gas flow through said first filter layer in order to control said gas sample flow through said first filter layer; and a test gas sensor; and at least one device selected from the group consisting of: a sealable test chamber arranged to receive a test object, a flange for connection of said gas probe to said test chamber, a tracer gas source, a tracer gas control unit, a tracer gas pressure regulator, a vacuum pump, a fixture for said test object and a fixture control unit.

* * * * *

UNITED STATES PATENT AND TRADEMARK OFFICE
CERTIFICATE OF CORRECTION

PATENT NO. : 8,627,710 B2 Page 1 of 1
APPLICATION NO. : 12/991212
DATED : January 14, 2014
INVENTOR(S) : Nylander et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 669 days.

Signed and Sealed this
Thirtieth Day of May, 2017

Michelle K. Lee
*Director of the United States Patent and Trademark Office*